US007632799B2

(12) United States Patent
Bach et al.

(10) Patent No.: US 7,632,799 B2
(45) Date of Patent: Dec. 15, 2009

(54) PROCESS FOR PREPARING COATED ENZYME GRANULES WITH SALT COATINGS

(75) Inventors: Poul Bach, Birkerod (DK); Ole Simonsen, Soborg (DK)

(73) Assignee: Novozymes A/S, Bagsvaerd (DK)

( * ) Notice: Subject to any disclaimer, the term of this patent is extended or adjusted under 35 U.S.C. 154(b) by 53 days.

(21) Appl. No.: 11/442,649

(22) Filed: May 26, 2006

(65) Prior Publication Data

US 2006/0247149 A1 Nov. 2, 2006

Related U.S. Application Data

(63) Continuation of application No. 10/499,497, filed as application No. PCT/DK02/00885 on Dec. 20, 2002, now abandoned.

(60) Provisional application No. 60/342,830, filed on Dec. 21, 2001.

(30) Foreign Application Priority Data

Dec. 21, 2001 (DK) .............................. 2001 01930

(51) Int. Cl.
*C11D 7/42* (2006.01)
*C12N 9/00* (2006.01)
*C12N 9/98* (2006.01)

(52) U.S. Cl. ...................... 510/441; 510/442; 510/392; 435/183; 435/187

(58) Field of Classification Search ................. 510/441, 510/442, 392; 252/186.25; 435/184, 183, 435/187
See application file for complete search history.

(56) References Cited

U.S. PATENT DOCUMENTS

| | | | | | |
|---|---|---|---|---|---|
| 3,691,090 | A | * | 9/1972 | Kitajima et al. | 427/213.36 |
| 3,953,354 | A | * | 4/1976 | Faust | 252/186.37 |
| 4,526,698 | A | * | 7/1985 | Kuroda et al. | 510/305 |
| 5,258,133 | A | * | 11/1993 | Chapple | 510/375 |
| 5,332,518 | A | * | 7/1994 | Kuroda et al. | 510/309 |
| 5,462,804 | A | * | 10/1995 | Kokubu et al. | 428/402.24 |
| 5,478,488 | A | * | 12/1995 | Doetsch et al. | 510/375 |
| 5,846,447 | A | * | 12/1998 | Beatty | 510/181 |
| 5,902,682 | A | * | 5/1999 | Bertsch-Frank et al. | 428/403 |
| 6,136,772 | A | * | 10/2000 | De Lima et al. | 510/392 |
| 6,239,095 | B1 | * | 5/2001 | Bertsch-Frank et al. | 510/375 |
| 6,268,329 | B1 | * | 7/2001 | Markussen | 510/392 |
| 6,348,442 | B2 | * | 2/2002 | Markussen | 510/392 |
| 6,465,408 | B1 | * | 10/2002 | Lee et al. | 510/349 |
| 6,602,841 | B1 | * | 8/2003 | Becker et al. | 510/392 |
| 6,602,843 | B2 | * | 8/2003 | Markussen | 510/392 |
| 6,641,866 | B2 | * | 11/2003 | Lee et al. | 427/213 |
| 6,849,590 | B1 | * | 2/2005 | Yamaboshi et al. | 510/441 |

FOREIGN PATENT DOCUMENTS

| | | |
|---|---|---|
| EP | 0 277 532 | 8/1988 |
| WO | WO 90/09428 | 8/1990 |
| WO | WO 94/24260 | 10/1994 |
| WO | WO 99/32595 | 7/1999 |
| WO | WO 00/01793 | 1/2000 |
| WO | WO 00/01793 A1 * | 1/2000 |

* cited by examiner

*Primary Examiner*—Lorna M Douyon
(74) *Attorney, Agent, or Firm*—Michael W. Krenicky

(57) ABSTRACT

The present invention relates to a process for preparing coated granules comprising the steps of: (a) providing a core unit comprising an active component (b) contacting the core unit with a liquid dispersion comprising a solvent, a dissolved salt and solid dispersed particles wherein the solid particles constitute at least 10% w/w of the total dry matter of the dispersion (c) evaporating the solvent of the liquid dispersion to leave salt and solid particles coated onto the core unit.

16 Claims, No Drawings

PROCESS FOR PREPARING COATED ENZYME GRANULES WITH SALT COATINGS

CROSS-REFERENCE TO RELATED APPLICATIONS

This application is a continuation of application Ser. No. 10/499,497 filed on Jun. 21, 2004 now abandoned, which is a 35 U.S.C. 371 national application of PCT/DK02/00885, filed Dec. 20, 2002, which claims priority or the benefit under 35 U.S.C. 119 of Danish application no. PA 2001 01930 filed Dec. 21, 2001 and U.S. provisional application No. 60/342,830 filed Dec. 21, 2001, the contents of which are fully incorporated herein by reference.

FIELD OF THE INVENTION

The present invention relates to a process for preparing coated particles and the use of said particles.

BACKGROUND OF THE INVENTION

It is known to the art to incorporate active components such as enzyme into dry solid particles or granules and thereby protect the active component from inactivation and/or protect the environment from the active component. Many granules are composed of a core unit comprising an active component upon which one or more layers of coating is applied to improve properties such as enzyme stability, dust formation, colour, solubility rate etc. Various coating compositions are known in the art including salts, which for example are known within the detergent industry to protect enzymes against bleach present in the detergents.

WO 00/01793 discloses a substantially continuous layer or coating encapsulating the core comprising a water-soluble compound, such as an inorganic salt.

WO 99/32595 discloses a granule including a core and a hydrated barrier material with moderate or high water activity, such as a salt.

The object of the present invention is to provide an improved method for coating core units with salt. Salt-coatings are usually applied to core units as liquid compositions where the solvent, e.g. water, is evaporated after the application, thereby leaving the salt on the core unit as a coating. Often large amounts of water need to be evaporated as many salts used in coatings have a limited solubility in water. If higher concentrations of salt in the liquid composition are attempted significant recrystallization take place creating large salt crystals which tend to block nozzles, pumps and valves making it difficult to use the process on an industrial basis.

The present invention solves this problem by increasing the amount of dry matter in the liquid salt composition applied to the core unit without increasing formation of large salt crystals.

SUMMARY OF THE INVENTION

In a first aspect the present invention relates to a process for preparing a coated granule comprising the steps of:

a) providing a core unit comprising an active component b) contacting the core unit with a liquid dispersion comprising a solvent, a dissolved salt and solid dispersed particles wherein the solid particles constitute at least 10% w/w of the total dry matter of the dispersion c) evaporating the solvent of the liquid dispersion to leave salt and solid particles coated onto the core unit.

In a second aspect the present invention relates to a coated granule obtainable by said process.

In a third aspect the present invention relates to a composition comprising the coated granule.

In a fourth aspect the present invention relates to the use of the coated granule for cleaning an object, for improving a feed or for improving a bread.

DETAILED DESCRIPTION

Definitions

The term "dispersion" is in the context of the present invention to be understood as a suspension of a discontinuous solid phase in a continuous liquid phase.

Thus the term "dispersed solid particles" is in the context of the present invention to be understood as said discontinuous solid phase in a continuous liquid phase.

The term "core unit" is in the context of the present invention to be understood as a particle or a granule comprising an active component.

The term "substantially active free" as used herein about a liquid dispersion is to be understood as less than 5 mg of active component per kg of dry matter.

The term "solubility" is in the context of the present invention to be understood as the amount of a compound in grams which can be dissolved in one liter of water at 25° C., 1 atm (ambient pressure).

The term "active component" is in the context of the present invention to be understood as all components, which when released from the coated granule in application of the coated granule in a process, serves a purpose of improving the process. Suitable active components are those which are either subject of deactivation and/or causing deactivation to other components in a composition comprising the granule.

The term "coating" is in the context of the present invention to be understood as a substantially continuous layer surrounding a particle and/or core unit.

The term "substantially continuous" in relation to a coating is in the context of the present invention to be understood as a coating having few or none holes, so that the core unit and/or granule it is encapsulating has few or none uncoated areas.

The Core Unit

The core unit contains the active component(s). Besides of the active component(s) the core unit may be constructed in any way or of any material which provides the desired functional properties of the core unit material, e.g. the core unit may consist of materials which allow readily release of the active component(s) upon introduction to an aqueous medium. In one particular embodiment the core unit is constructed of a particulate carrier (I) with the active component(s) absorbed and/or an active component(s) containing layer (II) applied on the carrier surface, optionally comprising a protecting reducing agent. There may even be additional coating within the core unit material providing desired functional properties of the core unit material. One particular core unit is the so called T-granulate wherein active component(s) and granulation material is mixed to form granules incorporating the active component(s) distributed throughout the core unit such as described in U.S. Pat. No 4,106,991 e.g. Example 1. Any conventional methods and non-active materials may be used to prepare the core unit. Examples of known conventional core units and materials is, inter alia, described in, U.S. Pat. No. 4,106,991 (in particular), EP 170360, EP 304332, EP 304331, EP 458849, EP 458845, WO 97/39116, WO 92/12645, WO 89/08695, WO 89/08694, WO 87/07292, WO 91/06638, WO 92/13030, WO 93/07260, WO 93/07263, WO 96/38527, WO 96/16151, WO 97/23606, U.S. Pat. No. 5,324, 649, U.S. Pat. No. 4,689,297, EP 206417, EP 193829, DE 4344215, DE 4322229 A, DD 263790, JP 61162185 A, JP 58179492, PCT/DK01/00627.

The core unit may be in any physical state, such as solid, liquid or gel. In a particular embodiment the core unit is in a solid state.

As a particular embodiment of the invention the core unit may be prepared by applying an active component layer onto a "placebo" carrier (active-free carrier) coated with a layer containing the active component according to the methodology described in e.g. WO 97/39116 or EP 0 193 829. Optionally additional active component may be absorbed into the surface of the carrier.

In one embodiment of the invention the core unit may be as the core unit described in WO 01/25412. Such core unit may, in terms of its relative mass, comprise up to about 30% w/w, such as up to about 20% w/w, in particular up to about 15% w/w, more particularly up to about 10% w/w, such as up to about 5% w/w of the overall mass of the finished granule.

In general the size of the core unit may, in terms of its diameter in its longest dimension, be no more than 2000 μm, particularly no more than 1200 μm, particularly no more than 700 μm or 600 μm, particularly between 300 and 1200 μm, more particularly between 500 and 600 μm even more particularly between 100 and 500 μm, such as between 100 and 400 μm, particularly between 200 and 300 μm. To prevent agglomeration of the enzyme core unit during further processing however, the size of the enzyme core unit may in particular be greater than 50 μm, such as greater than 100 μm.

The core unit may comprise excipients or additives, which may serve a specialised function in the core unit. Excipients may be compounds conventionally used in the art and the type will depend on the active component. Examples of excipients and additives include:

Enzyme stabilising agents. Enzyme stabilising or protective agents such as conventionally used in the field of granulation may be elements of the enzyme-containing core unit. Stabilising or protective agents may fall into several categories: acid, alkaline or neutral materials, reducing agents, antioxidants and/or salts of first transition series metal ions. Each of these may be used in conjunction with other protective agents of the same or different categories. Examples of alkaline protective agents are alkali metal silicates, carbonates or bicarbonates which provide a chemical scavenging effect by actively neutralising e.g. oxidants. Examples of reducing protective agents are salts of sulfite, thiosulfite or thiosulfate, while examples of antioxidants are methionine, butylated hydroxytoluene (BHT) or butylated hydroxyanisol (BHA). In particular agents may be salts of thiosulfates, e.g. sodium thiosulfate or methionine. Also enzyme stabilizers may be borates, borax, formates, di- and tricarboxylic acids and reversible enzyme inhibitors such as organic compounds with sulfhydryl groups or alkylated or arylated boric acids. Examples of boron based stabilizer may be found in WO 96/21716, whereas a particular boron based stabilizer is 4-Formyl-Phenyl-Boronic Acid or derivatives thereof described in WO 96/41859 both disclosured incorporated herein by reference. Still other examples of useful enzyme stabilizers are gelatine, casein, Poly vinyl pyrrolidone (PVP) and powder of skimmed milk. Enzyme stabilising agents or protective agents may be 0.01-10% w/w of the core unit, particularly 0.1-5%, e.g. 0.5-2.5% w/w of the core unit.

Solubilising agents. The solubility of the core unit is critical, e.g. in cases where the active component is an enzyme and the unit is a component of detergent formulation. As is known by the person skilled in the art, many agents, through a variety of methods, serve to increase the solubility of formulations, and typical agents known to the art can be found in national Pharmacopeia's. Thus, the core unit may optionally comprise any agent that serves to enhance the solubility of the active. These agents usually cause the granule to swell upon contact with water, or to disintegrate, rupture, burst or break open.

Inorganics, such as water soluble and/or insoluble inorganic salts such as finely ground alkali sulphate, alkali carbonate and/or alkali chloride, clays such as kaolin (e.g. Speswhite™, English China Clay), bentonites, talcs, zeolites, calcium carbonate, and/or silicates.

Binders, e.g. binders with a high melting point or indeterminately high melting points and of a non-waxy nature, e.g. polyvinyl pyrrolidone, dextrins, polyvinylalcohol, cellulose derivatives, for example methyl hydroxypropyl cellulose, methyl cellulose or CMC. A suitable binder is a carbohydrate binder such as Glucidex 21D™ available from Roquette Freres, France.

Waxes, such as organic compounds having a melting temperature of 25-150° C., particularly 35-80° C. Suitable waxes includes Poly ethylene glycols; polypropylens or polyethylenes or mixtures thereof; Nonionic surfactants; Waxes from natural sources such as Carnauba wax, Candelilla wax, bees wax, hydrogenated plant oil or animal tallow; fatty acid alcohols; mono-glycerider and/or di-glycerider and/or tri-glycerides; fatty acids and paraffines.

Fibre materials such as pure or impure cellulose in fibrous form. This can be sawdust, pure fibrous cellulose, cotton, or other forms of pure or impure fibrous cellulose. Also, filter aids based on fibrous cellulose can be used. Several brands of cellulose in fibrous form are on the market, e.g. CEPO™ and ARBOCELL™. Pertinent examples of fibrous cellulose filter aids are is Arbocel BFC200™ and Arbocel BC200™. Also synthetic fibres may be used as described in EP 304331 B1 and typical fibres may be made of polyethylene, polypropylene, polyester, especially nylon, polyvinylformate, poly (meth)acrylic compounds.

Cross-linking agents such as enzyme-compatible surfactants, e.g. ethoxylated alcohols, especially ones with 10 to 80 ethoxy groups. These may both be found in the coating and in the core unit.

Dispersing agents e.g. for improving dispersion during wet milling, mediators e.g. for boosting bleach action upon dissolution of the granule in e.g. a washing application, and and/or solvents may be incorporated as conventional granulating agents. Suitable dispersing agent can be but are not limited to polyacrylates, polycarboxylates, polyphosphates (e.g. tripolyphosphate) etc. and salts hereof, e.g. ammonia, potassium, magnesium, calcium or sodium salts such as Sodium Tri Poly Phosphates (STPP).

Viscosity regulating agents. Viscosity regulating agents may be present in the core unit as reminiscence from the preparation of the core unit. Suitable viscosity regulating agents can be but are not limited to ammonia salts of poly acrylates and Sodium Tri Poly Phosphates (STPP).

If the core unit is small in size such as described in WO 01/25412 an important feature of the core unit is that the volume, in which excipients are contained, is much smaller than the volume of core units known in the art. Accordingly, for a calculated optimum concentration of an excipient in a core unit the absolute amount of excipient required to obtain this concentration is reduced. This feature reduces the manufacturing costs of a coated granule of the invention, especially when the excipients are expensive specialty chemicals.

The core unit may through the coating absorb moisture from the surrounding environment, a process which may cause the core unit to swell resulting in crack formation in the coating and further moisture absorbance. The core unit may even in at high relative humidity dissolve and become fluid. Accordingly in order to provide further stabilization of the active component the core unit may in particular be a non absorbing core, i.e. it may only be able of absorbing less moisture than 20% w/w of it own dry weight, particularly less than 10% w/w, e.g. less than 8% w/w or less than 5% w/w, measured at 75% RH (where % RH is the relative humidity of air, thus 100% RH is air saturated with water moisture at a fixed temperature and % RH thus reflects the percent moisture saturation of the air) at 20° C.

The Liquid Dispersion

The liquid dispersion comprises a solvent, a dissolved salt and dispersed solid particles. It is an advantage if the content of dry matter in the liquid dispersion is high because then less solvent needs to be evaporated after application of the liquid dispersion to the core unit. One way of obtaining a liquid dispersion with decreased solvent content is to prepare a liquid dispersion by wet milling, by wet milling the particles get smaller and therefore it is possible to obtain a larger amount of particles in the liquid dispersion. The optimal range of content of dry matter will depend on the type of dissolved salt and dispersed solid particles. However, it is contemplated that the liquid dispersion will have a content of dry matter of at least 10% w/w, e.g. in the range of 10-90% w/w, or in the range of 10-80% w/w or in the range of 10-70% w/w, in particular at least 20% w/w, e.g. in the range of 20-90% w/w, or in the range of 20-80% w/w, or in the range of 20-70% w/w, or more particularly at least 40% w/w, e.g. in the range of 40-90% w/w, or in the range 40-80% w/w, or in the range of 40-70% w/w, or more particularly at least 60% w/w, e.g. in the range of 60-90% w/w, or in the range of 60-80% w/w, or in the range of 60-70% w/w, or more particularly at least 70% w/w, e.g. in the range of 70-90% w/w, or in the range of 70-80% w/w, or more particularly at least 80% w/w, e.g. in the range of 80-90% w/w, or more particularly at least 90% w/w or even more particularly at least 95% w/w.

In one embodiment of the invention the liquid dispersion may be saturated with salt.

The liquid dispersion is applied to the core unit and the solvent is evaporated thereby leaving the dry matter of the liquid dispersion on the core unit as a substantially continuous layer covering the core unit. Thus the dry matter of the liquid dispersion creates the coating of the core unit.

Solvent

In one embodiment of the invention the solvent is water, i.e. the liquid dispersion is an aqueous dispersion. The liquid dispersion may comprise other agents, e.g. agents which make the liquid dispersion easier to apply to the core unit or agents which are relevant for the functional characteristics of the coating. Such agents include dispersing agents, viscosity regulating agents or sugars, such as sucrose or glucose. Other examples of agents which may be present in the liquid dispersion includes the compounds/agents mentioned in the core unit section above.

Dissolved Salt

The dissolved salt may be an inorganic salt, e.g. salts of sulfate, sulfite, phosphate, phosphonate, nitrate, chloride or carbonate or salts of simple organic acids (less than 10 carbon atoms e.g. 6 or less carbon atoms) such as citrate, malonate or acetate. Examples of cations in these salt are alkali or earth alkali metal ions, although the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. Specific examples include $NaH_2PO_4$, $Na_2HPO_4$, $Na_3PO_4$, $(NH_4)H_2PO_4$, $KH_2PO_4$, $K_2HPO_4$, $ZnSO_4$, $Na_2SO_4$, $K_2SO_4$, $KHSO_4$, $ZnSO_4$, $MgSO_4$, $CuSO_4$, $Mg(NO_3)_2$, $(NH_4)_2SO_4$, sodium borate, magnesium acetate and sodium citrate.

The dissolved salt may also be a hydrated salt, i.e. a crystalline salt hydrate with bound water(s) of crystallization, such as described in WO 99/32595. Examples of hydrated salts include magnesium sulfate heptahydrate ($MgSO_4(7H_2O)$), zinc sulfate heptahydrate ($ZnSO_4(7H_2O)$), copper sulfate pentahydrate ($CuSO_4(5H_2O)$), sodium phosphate dibasic heptahydrate ($Na_2HPO_4(7H_2O)$), magnesium nitrate hexahydrate ($Mg(NO_3)_2(6H_2O)$), sodium borate decahydrate, sodium citrate dihydrate and magnesium acetate tetrahydrate.

The solubility of the dissolved salt will typically be above 0.1 g/liter, e.g. in the range of 0.1 g/liter-2 kg/liter, or in the range of 0.1 g/liter-1.5 kg/liter or in the range of 0.1 g/liter-1 kg/liter in particular above 1 g/liter, e.g. in the range of 1 g/liter-2 kg/liter, or in the range of 1 g/liter-1.5 kg/liter or in the range of 1 g/liter-1 kg/liter or more particularly above 10 g/liter, e.g. in the range of 10 g/liter-2 kg/liter, or in the range of 10 g/liter-1.5 kg/liter or in the range of 10 g/liter-1 kg/liter, such as in the range of 100-1000 g/liter, or 500-1500 g/liter, or 300-900 g/liter, particularly 300-500 g/liter or 500-900 g/liter.

In one embodiment of the present invention the salt used in the liquid dispersion may have in its solid and/or crystalline state a high constant humidity as it is expected that this feature may inhibit moisture form entering the core unit. The term "constant humidity" (in the context of the present invention sometimes abbreviated as CH) of a compound or substance is to be understood as the % RH of atmospheric air in equilibrium with a saturated aqueous solution of said compound in contact with the solid phase of said compound, all confined within a closed space at a given temperature. This definition is in accordance with "*Handbook of chemistry and physics*" CRC Press, Inc., Cleveland, USA, 58th edition, p E46, 1977-1978. The term "% RH" is to be understood as the relative humidity of air. 100% RH is air saturated with water moisture at a fixed temperature and % RH thus reflects the percent moisture saturation of the air. Accordingly $CH_{20° C.}$=50% for a compound means that air with a 50% humidity will be in equilibrium with a saturated aqueous solution of the compound at 20° C. Accordingly the term constant humidity is a measure of the hygroscopic properties of a compound. In particular the constant humidity may be above 50, such as above 60%, more specifically above 70%, or above 80%, or above 90% or above 95%.

Dispersed Solid Particles

The presence of solid dispersed particles in the liquid dispersion increases the content of dry matter therein, which result in that less solvent has to be evaporated subsequently. Furthermore, the presence of dispersed solid particles in the coating prevents formation of large salt crystals which tends to block nozzles, tubes etc in the equipment. Without being bound to any theory we believe that the dispersed solid particles act as seed upon which the salt crystallizes forming small particles which are so small that they do not block the equipment and at the same prevent formation of large salt crystals.

Thus it is important that the solid dispersed particles should not be too large as that may make them block equipment making it difficult to apply the liquid dispersion to the core unit. Furthermore, too large solid particles may make the coating susceptible to cracks and thereby create canals through which compounds from the surroundings can enter the core unit and/or the active component can diffuse to the surrounding environment. Thus the solid dispersed particles should have a size in the longest dimension less than the thickness of the coating. In particular the size may be less than 20 μm, particularly less than 10 μm, more particularly less than 5 μm, more particularly less than 2 μm or even more particularly less than 1 μm, such as in the range of 0.6-20 μm or in the range of 0.1-0.3 μm.

One way of obtaining small particles in the dispersion is by wet milling, one advantage of using wet milling is that the nozzles do not get blocked, another advantage of wet milling is the energy consumption used to obtain very small particles are much smaller than dry milling, a further advantage is that it is possible to prepare a thinner coating compared to ordinary salt coatings and the coating prepared from salt particles prepared by wet milling is more efficient as a diffusion barrier.

Examples of solid dispersed particles include inorganic or organic compounds. Among inorganic compounds particularly salts, such as those described above in the section "dissolved salt", e.g. $Na_2SO_4$, $MgSO_4$, e.g. in the form of $MgSO_4(7H_2O)$ and/or $CaCO_3$ are useful as solid dispersed particles. In a particular embodiment of the present invention the solid dispersed particles consist at least in part of the same salt as the dissolved salt. In a more particular embodiment of the present invention the solid dispersed particles are the same salt as the dissolved salt.

In a particular embodiment of the present invention the solid dispersed particles are selected from the group consisting of $NaH_2PO_4$, $Na_2HPO_4$, $Na_3PO_4$, $(NH_4)H_2PO_4$, $KH_2PO_4$, $K_2HPO_4$, $ZnSO_4$, $Na_2SO_4$, $K_2SO_4$, $KHSO_4$, $ZnSO_4$, $MgSO_4$, $CuSO_4$, $Mg(NO_3)_2$, $(NH_4)_2SO_4$, sodium borate, magnesium acetate, sodium citrate, magnesium sulfate heptahydrate ($MgSO_4(7H_2O)$), zinc sulfate heptahydrate ($ZnSO_4(7H_2O)$), copper sulfate pentahydrate ($CuSO_4(5H_2O)$), sodium phosphate dibasic heptahydrate ($Na_2HPO_4(7H_2O)$), magnesium nitrate hexahydrate ($Mg(NO_3)_2(6H_2O)$), sodium borate decahydrate, sodium citrate dihydrate and magnesium acetate tetrahydrate.

Other examples of inorganic compounds useful as solid dispersed particles include clays such as kaolin, bentonite, talc, silicates, lime, chalk or other minerals or $TiO_2$. Among organic compounds various starches are useful, such as starch from: cassava [notably from bitter cassava (*Manihot esculenta*) or sweet cassava (*Manihot dulcis*)]; sago-palm (*Metroxylon* spp., such as *M. sagu*); potato (*Solanum tuberosum*); rice (*Oryza* spp.); corn (*maize, Zea mays*); wheat (*Triticum* spp.); barley (*Hordeum* spp., such as *H. vulgare*) sweet potato (*Ipomoea batatas*); sorghum (*Sorghum* spp.); yam (*Dioscorea* spp.); rye (*Secal cereale*); oat (*Avena* spp., such as *A. sativa*); millet (e.g. from species of *Digitaria, Panicum, Paspalum, Pennisetum* or *Setaria*); buckwheat (*Fagopyrum* spp., such as *F. esculentum*); waxy maize; other cereals; arrowroot (e.g. *Maranta arundinacea*); taro (*Colocasia* spp., such as *C. antiquorum* or *C. esculenta*); tannia (*Xanthosoma sagittifolium*); *Amaranthus* spp.; and *Chenopodium* spp. The starch may in a particular embodiment be grinded to a suitable particle size.

It is envisaged that if the amount of solid dispersed particles is too low it may not have the desired effect on the coating process but also that if it is too high the coating will not be optimal, i.e. it may be difficult to apply. Thus the solid dispersed particles should constitute at least 10% w/w of the total dry matter of the dispersion, in particular at least 20% w/w, more particularly at least 30% w/w, more particularly at least 40% w/w, more particularly at least 50% w/w, more particularly at least 60% w/w, more particularly at least 70% w/w, or even more particularly at least 80% w/w of the total dry matter of the dispersion.

In a particular embodiment of the present invention the solid dispersed particles are salt particles and said salt particles should constitute at least 25% w/w of the total dry matter of the dispersion, in particular 50% w/w, more particularly at least 75%.

In a particular embodiment of the present invention the solid dispersed particles are Kaolin.

The liquid dispersion may further comprise other components such as the excipients and additives as mentioned vide supra; enzyme stabilizing agents, solubilising agents, inorganics, binders, waxes, fibre materials, cross-linking agents, dispersing agents and viscosity regulating agents. Besides these components the coating may further comprise pigments and lubricants. Suitable pigments include, but are not limited to, finely divided whiteners, such as titanium dioxide or kaolin, coloured pigments, water soluble colorants, as well as combinations of one or more pigments and water soluble colorants.

As used in the present context, the term "lubricant" refers to any agent which reduces surface friction, lubricates the surface of the granule, decreases tendency to build-up of static electricity, and/or reduces friability of the granules. Lubricants can also play a related role in improving the coating process, by reducing the tackiness of binders in the coating. Thus, lubricants can serve as anti-agglomeration agents and wetting agents.

Examples of suitable lubricants are polyethylene glycols (PEGs) and ethoxylated fatty alcohols.

In an especially preferred embodiment of the invention, only a lubricant is applied as additional coating. The composition of 1) an enzyme containing core, 2) a coating and 3) and an additional lubricant coating has shown particularly good properties with respect to enzyme stability.

The liquid dispersion may also comprise other components which have a specialized function in the coating, such as minor amounts of a protective agent capable of reacting with a component capable of inactivating (being hostile to) the active component. The protective agent may thus e.g. be capable of neutralizing, reducing or otherwise reacting with the hostile component rendering it harmless to the active component. If the active component is an enzyme typical components capable of inactivating the active component are oxidants such as perborates, percarbonates, organic peracids and the like.

Protective agents may fall into several categories: alkaline or neutral materials, reducing agents, antioxidants and/or salts of first transition series metal ions. Each of these may be used in conjunction with other protective agents of the same or different categories. Examples of alkaline protective agents are alkali metal silicates, -carbonates or bicarbonates which provide a chemical scavenging effect by actively neutralizing e.g. oxidants. Examples of reducing protective agents are salts of sulfite, thiosulfite or thiosulfate, while examples of antioxidants are methionine, butylated hydroxytoluene (BHT) or butylated hydroxyanisol (BHA). In particular protective agents may be salts of thiosulfates, e.g. sodium thiosulfate.

Coated Granules

The coating, which is here to be understood as the layer surrounding the core unit after application of the liquid dispersion and evaporating the solvent, may in a particular embodiment comprise at least 60% w/w, e.g. 65% w/w or 70% w/w salt, which in particular may be at least 75% w/w, e.g. at least 80% w/w, at least 85% w/w, e.g. at least 90% w/w or at least 95% w/w.

Depending on the size of the core material the coating may be applied in 1-75% w/w of the weight of the coated granule to obtain a desired size of the coated granule.

Usually coatings constitute 2-40% w/w, particularly 3-10% w/w, e.g. 6% of the coated granule.

However for small sizes of core material (see the paragraph on core units and below) the coating may be applied in 50-75% w/w or 15-50% of the coated granule.

In one embodiment the coated granule is a granule according to WO 01/25412, where the core unit is smaller than core units known to the art and the coating is thicker than coating known to the art. For such granules the ratio between the diameter of the coated granule and the diameter of the core unit (abbreviated $D_G/D_C$) for this type of granules will usually be $D_G/D_C$ is at least 1.1, particularly at least 1.5, more particularly at least 2, more particularly at least 2.5, more particularly at least 3, most particularly at least 4. $D_G/D_C$ is however particularly below about 100, particularly below about 50, more particularly below 25, and most particularly below 10. A particularly range for $D_G/D_C$ is about 4 to about 6. Thus for such granules the thickness of the coating should be at least 25 μm. A particular thickness is at least 50 μm such as at least 75 μm, at least 100 μm, at least 150 μm, at least 200 μm, at least 250 μm or particularly at least 300 μm.

The coating should encapsulate the core unit by forming a substantially continuous layer. A substantially continuous layer is to be understood in the present invention as a coating having few or none holes, so that the core unit it is encapsulating has few or none uncoated areas. The layer or coating should in particular be homogenous in thickness.

As mentioned above in the section of "the liquid dispersion" protective agents may also be present in the coating, usually constituting between 1-40% w/w of the coating, particularly 5-30%, e.g. 10-20%.

Active Components

The active component of the invention may be any active component or mixture of active components, which benefits from being separated from the environment surrounding the particle. The term "active component" is meant to encompass all components, which upon release from the particle upon applying the particle of the invention in a process serves a purpose of improving the process. Suitable active components are those, which are either subject of deactivation and/or causing deactivation to other components in the compositions of the invention. As said the active component may be present dispersed as discrete solid particles in the core particle.

The active component may be inorganic of nature, such as bleach components, or organic. In particular active components are active biologically materials, such as catalytically active materials such as enzymes, pharmaceutical materials active in the human or animal body or agricultural chemicals such as herbicides, pesticides, bactericides and/or fungicides. Such compounds are usually very sensitive to the surrounding environment and may benefit from being embedded in a granule. It may be obtained from chemical processes or from fermenting microorganisms. In particular active components may be peptides or polypetides such as enzymes.

The enzyme in the context of the present invention may be any enzyme or combination of different enzymes, which benefits from being granulated and thus be protected against a hostile environment in order to be applicable for a specific use. Accordingly, when reference is made to "an enzyme" this will in general be understood as including combinations of one or more enzymes.

It is to be understood that enzyme variants (produced, for example, by recombinant techniques) are included within the meaning of the term "enzyme". Examples of such enzyme variants are disclosed, e.g., in EP 251,446 (Genencor), WO 91/00345 (Novo Nordisk A/S), EP 525,610 (Solvay) and WO 94/02618 (Gist-Brocades NV).

The enzyme classification employed in the present specification with claims is in accordance with *Recommendations* (1992) *of the Nomenclature Committee of the International Union of Biochemistry and Molecular Biology*, Academic Press, Inc., 1992.

Accordingly the types of enzymes which may appropriately be incorporated in granules of the invention include oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6. -.-.-).

Examples of oxidoreductases which may be used in the context of the invention include peroxidases (EC 1.11.1), laccases (EC 1.10.3.2) and glucose oxidases (EC 1.1.3.4)], while examples of transferases are transferases in any of the following sub-classes:

Transferases transferring one-carbon groups (EC 2.1);
transferases transferring aldehyde or ketone residues (EC 2.2); acyltransferases (EC 2.3);
glycosyltransferases (EC 2.4);
transferases transferring alkyl or aryl groups, other that methyl groups (EC 2.5); and
transferases transferring nitrogenous groups (EC 2.6).

A particular type of transferase in the context of the invention is a transglutaminase (protein-glutamine γ-glutamyltransferase; EC 2.3.2.13).

Further examples of suitable transglutaminases are described in WO 96/06931 (Novo Nordisk A/S).

Examples of hydrolases which may be used in the context of the invention are: Carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fall within a group denoted herein as "carbohydrases"), such as alpha-amylases (EC 3.2.1.1); peptidases (EC 3.4, also known as proteases); and other carbonyl hydrolases].

In the present context, the term "carbohydrase" is used to denote not only enzymes capable of breaking down carbohydrate chains (e.g. starches) of especially five- and six-membered ring structures (i.e. glycosidases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses): alpha-amylases (3.2.1.1), beta-amylases (3.2.1.2), glucan 1,4-alpha-glucosidases (3.2.1.3), cellulases (3.2.1.4), endo-1,3(4)-beta-glucanases (3.2.1.6), endo-1,4-beta-xylanases (3.2.1.8), dextranases (3.2.1.11), chitinases (3.2.1.14), polygalacturonases (3.2.1.15), lysozymes (3.2.1.17), beta-glucosidases (3.2.1.21), alpha-galactosidases (3.2.1.22), beta-galactosidases (3.2.1.23), amylo-1,6-glucosidases (3.2.1.33), xylan 1,4-beta-xylosidases (3.2.1.37), glucan endo-1,3-beta-D-glucosidases (3.2.1.39), alpha-dextrin endo-1,6-alpha-glucosidases (3.2.1.41), sucrose alpha-glucosidases (3.2.1.48), glucan endo-1,3-alpha-glucosidases (3.2.1.59), glucan 1,4-beta-glucosidases (3.2.1.74), glucan endo-1,6-beta-glucosidases (3.2.1.75), arabinan endo-1,5-alpha-L-arabinosidases (3.2.1.99), lactases (3.2.1.108), chitosanases (3.2.1.132) and xylose isomerases (5.3.1.5).

Examples of commercially available oxidoreductases (EC 1.-.-.-) include GLUZYME™ (enzyme available from Novo Nordisk A/S).

Examples of commercial proteases (peptidases) include ESPERASE™, ALCALASE™, NEUTRASE™, DURAZYM™, SAVINASE™, KANNASE™, PYRASE™, Pancreatic Trypsin NOVO (PTN), BIO-FEED™ PRO and CLEAR-LENS™ PRO (Novozymes A/S).

Other commercial proteases include MAXATASE™, MAXACAL™, MAXAPEM™, OPTI-CLEAN™ and PURAFEC™ (Genencor International Inc. or Gist-Brocades).

Examples of commercial lipases include LIPOLASE™, LIPOLASE™ ULTRA, LIPOPRIME, LIPOZYME™, PALATASE™, NOVOZYM™ 435 and LECITASE™ (Novozymes A/S).

Other commercial lipases include LUMAFAS™ (*Pseudomonas mendocina* lipase from Genencor International Inc.); LIPOMAX™ (*Ps. pseudoalcaligenes* lipase from Gist- brocades/Genencor Int. Inc.; and *Bacillus* sp. lipase from Solvay enzymes.

Examples of commercial carbohydrases include ALPHA-GAL™, BIO-FEED™ ALPHA, BIO-FEED™ BETA, BIO-FEED™ PLUS, BIO-FEED™ PLUS, NOVOZYME™ 188, CELLUCLAST™, CELLUSOFT™, CEREMYL™, CITROZYM™, DENIMAX™, DEZYME™, DEXTROZYME™, FINIZYM™, FUNGAMYL™, GAMANASE™, GLUCANEX™, LACTOZYM™, MALTOGENASE™, PENTOPAN™, PECTINEX™, PROMOZYME™, PULPZYME™, NOVAMYL™, TERMAMYL™, AMG™ (AMYLOGLUCOSIDASE NOVO), MALTOGENASE™, SWEETZYME™ and AQUAZYM™ (Novozymes A/S).

The amount of enzyme to be incorporated in a granule of the invention will depend on the intended use of the granulate. For many applications, the enzyme content will be as high as possible or practicable.

The content of enzyme (calculated as pure enzyme protein) in a coated granule of the invention will typically be in the range of from about 0.5% to 20% by weight of the core unit.

However, if the core unit is to be as small as possible as described above, e.g. as in WO 01/25412 the content of enzyme by weight of the core will usually be higher so that there is enough enzyme present to make the granule industrial applicable. Thus the enzyme content (calculated as pure enzyme protein) in a core unit for small cores will typically be in the range of from about 20% to 100% by weight of the enzyme core unit, preferably no less than 25%, such as no less than 30%, 35%, 40%, 45%, 50%, 55%, 60%, 65%, 70%, 75%, 80%, 85% 90%, or 95% by weight. However some enzymes have a very high specific activity so that less enzyme protein by weight is required to maintain a high activity of the core unit.

The enzymatic activity of the coated granule will depend on the enzyme but for example when a protease (or peptidase) is incorporated in granules of the invention the enzyme activity (proteolytic activity) of the coated granules will typically be in the range of 1-50 KiloNovoProteaseUnits per gram. Likewise, in the case of, for example, $\alpha$-amylases, an activity of 10-500 KiloNovoUnits per gram will be typical, whilst for lipases, an activity in the range of 50-400 KiloLipolaseUnits per gram will normally be suitable. All units are known to the art.

Additional Coatings

The granules of the present invention may comprise one, two or more additional coating layers on the inside or outside surface of the protective coating according to the invention.

The additional coating layers may perform any of a number of functions in the granule, depending on the intended use of the granule. Thus, for example, an additional coating may achieve one or more of the following effects:

(i) further reduction of the dust-formation tendency of a granule;

(ii) further protection of enzyme(s) in the granule against oxidation by bleaching substances/systems (e.g. perborates, percarbonates, organic peracids, alkaline agents or other reactive components);

(iii) dissolution at a desired rate upon introduction of the granule into a liquid medium (such as an aqueous medium);

(iv) provide a better physical strength of the granule.

Any additional conventional coating(s) of desired properties may be applied and examples of conventional coating materials and coating methods is, inter alia, described in U.S. Pat. No. 4,106,991, EP 170360, EP 304332, EP 304331, EP 458849, EP 458845, WO 97/39116, WO 92/12645, WO 89/08695, WO 89/08694, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229 A, DD 263790, JP 61162185 A, JP 58179492 or PCT/DK/01/00628.

In appropriate embodiments of granules according to the present invention, the additional coating layer may be composed as described in U.S. Pat. No. 4,106,991, see e.g. example 22 [e.g. with a waxy material such as polyethylene glycol (PEG), optionally followed by powdering with a whitener such as titanium dioxide].

Additional coating layers may further comprise one or more of the following: anti-oxidants, chlorine scavengers, plasticizers, pigments, lubricants (such as surfactants or antistatic agents) additional enzymes and fragrances.

Plasticizers useful in coating layers in the context of the present invention include, for example: polyols such as sugars, sugar alcohols, or polyethylene glycols (PEGs) having a molecular weight less than 1000; urea, phthalate esters such as dibutyl or dimethyl phthalate; and water.

Suitable pigments include, but are not limited to, finely divided whiteners, such as titanium dioxide or kaolin, coloured pigments, water soluble colorants, as well as combinations of one or more pigments and water soluble colorants.

As used in the present context, the term "lubricant" refers to any agent which reduces surface friction, lubricates the surface of the granule, decreases tendency to build-up of static electricity, and/or reduces friability of the granules. Lubricants can also play a related role in improving the coating process, by reducing the tackiness of binders in the coating. Thus, lubricants can serve as anti-agglomeration agents and wetting agents.

In one embodiment of the invention the granule may in addition to the coating(s) comprise a lubrication layer on the outer surface of the layer as describe in PCT/DKO1/00582. The lubricant is a compound or a mixture of compounds forming a non-aqueous liquid at 25° C. and which preferably has a viscosity of less than 10000 centipoises at 25° C., such as 500-10000 cP, particularly less than 4000 centipoises such as 500-4000 cP, more particularly less than 3000 centipoises such as 500-3000 cP and most particularly less than 2500 centipoises such as 500-2500 cP. The lubricated granules may have a relative friction coefficient which is less than 80%, e.g. 5-80%, when compared to unlubricated granules when measured by a rheometer by using a tip speed of 50 rpm, a helix angle of 3° (compaction mode), using the 46 mm rotor and weighing 170 g granulate into a 50 mm testing container. In particular, the relative friction coefficient is less than 78%, e.g. 5-78%, more particularly less than 75%, e.g. 5-75%, most particularly less than 70%, e.g. 5-70%, compared to unlubricated granules. The lubricant may be an organic compound or a mixture of organic compounds that satisfy the low viscosity requirements. In particular lubricants may be nonionic surfactants such as Softanol (e.g. Softanol 50) and/or Dobanol, natural refined mineral oils such as Whiteway T15 (an alkane oil), synthetic mineral oils, such as silicone oils, animal oils, plant oil or any suitable mixture. In one embodiment the lubricant and the coating material may be mixed prior to the application of lubricant and coating to the granules. This mixture or dispersion may thus be applied simultaneously to the granule and because of the insolubility of the lubricant in the coating material the lubricant may separate from the coating material to form an outer lubrication layer. In particular the lubricant may be a mineral oil having a viscosity of less than 10000 centipoises which reduces the relative friction coefficient of lubricated granules to less than 80% when compared to unlubricated granules. To prevent agglomeration and/or stickiness of the granules to become a problem in handling granules comprising an active component and to avoid the cost and problems of adding various anti-agglomeration agents, the lubricant may be applied in a very thin layer constituting less than 1% of the granule by weight, such as between 0.01% to 1% particularly less than 0.75% w/w, such as between 0.1% to 0.75%, more particularly about 0.5% w/w such as between 0.1% to 0.5% of the granule. The granules may be free of anti-caking agents applied on the lubrication layer.

Other examples of suitable lubricants are polyethylene glycols (PEGs) and ethoxylated fatty alcohols.

In an especially particular embodiment of the invention, only a lubricant is applied as additional coating. The composition of 1) an enzyme containing core, 2) a coating and 3) and an additional lubricant coating has shown particularly good properties with respect to enzyme stability.

Methods of Preparing Coated Particles

Without being limited to this theory we believe that the dispersed solid particles in the coating composition act as seeds upon which the salt crystallizes, creating small salt-crystals and thereby preventing the salt from re-crystallizing into large salt crystals which tend to block nozzles, pumps, valves and other equipment during application of the coating.

Preparing the Core Unit

Methods for preparing the core include known enzyme granule formulation technologies, i.e.:

a) Spray dried products, wherein a liquid enzyme-containing solution is atomised in a spray drying tower to form small droplets which during their way down the drying tower dry to form an enzyme-containing particulate material. Very small particles can be produced this way (Michael S. Showell (editor); Powdered detergents; Surfactant Science Series; 1998; vol. 71; page 140-142; Marcel Dekker).

b) Layered products, wherein the enzyme is coated as a layer around a pre-formed inert core particle, wherein an enzyme-containing solution is atomised, typically in a fluid bed apparatus wherein the pre-formed core particles are fluidised, and the enzyme-containing solution adheres to the core particles and dries up to leave a layer of dry enzyme on the surface of the core particle. Particles of a desired size can be obtained this way if a useful core particle of the desired size can be found. This type of product is described in e.g. WO 97/23606 c) Absorbed core particles, wherein rather than coating the enzyme as a layer around the core, the enzyme is absorbed onto and/or into the surface of the core. Such a process is described in WO 97/39116.

d) Extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme. (Michael S. Showell (editor); Powdered detergents; Surfactant Science Series; 1998; vol. 71; page 140-142; Marcel Dekker)

e) Prilled products, wherein an enzyme powder is suspended in molten wax and the suspension is sprayed, e.g. through a rotating disk atomiser, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. Also U.S. Pat. No. 4,016,040 and U.S. Pat. No. 4,713,245 are documents relating to this technique f) Mixer granulation products, wherein an enzyme-containing liquid is added to a dry powder composition of conventional granulating components. The liquid and the powder in a suitable proportion are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 (NOVO NORDISK) and related documents EP 170360 B1 (NOVO NORDISK), EP 304332 B1 (NOVO NORDISK), EP 304331 (NOVO NORDISK), WO 90/09440 (NOVO NORDISK) and WO 90/09428 (NOVO NORDISK). In a particular product of this process wherein various high-shear mixers can be used as granulators, granulates consisting of the enzyme, fillers and binders etc. are mixed with cellulose fibres to reinforce the particles to give the so-called T-granulate. Reinforced particles, being more robust, release less enzymatic dust (vide infra).

Preparation of the Liquid Dispersion

One object of the invention resides in a preparation of a dispersion having on one side a hitherto unforeseen content of dry matter, while still being spray-able on a core unit. In that respect the size of the solid dispersed particles is important.

In order to control the size of the dispersed particles, the liquid dispersion may be prepared by (1) preparing a saturated solution of a desired salt and (2) adding a sufficient amount of solid particles to be dispersed.

In particular embodiment the solid particles to be dispersed are seed particles onto which the dissolved salt can crystallize. In this embodiment additional salt may be added to the dispersion after addition of the seed particles without formation of large re-crystallization products, which prevents coating of the core unit. Thus a significant in the dry matter contents can be achieved without the drawbacks of prior art methods.

Further, it has surprisingly been found that small molecular weight sugars, such as sucrose and glucose decrease the viscosity of the highly concentrated liquid dispersion, further facilitating applying the coating on the core unit.

In a particular embodiment of the present invention the liquid dispersion is prepared by wet milling.

Coating of a Granule

The invention relates to a process for preparing a coated particle/granule comprising the steps of:

A process for preparing a coated granule comprising the steps of:

a) providing a core unit comprising an active component
b) contacting the core unit with a liquid dispersion comprising a solvent, a dissolved salt and solid dispersed particles wherein the solid particles constitute at least 10% w/w of the total dry matter of the dispersion
c) evaporating the solvent of the liquid dispersion to leave salt and solid particles coated onto the core unit In one embodiment of the invention the coated granule may be produced by a fluid bed process comprising:

a) fluidising the core unit in a fluid bed apparatus,
b) introducing the liquid dispersion comprising a solvent, a dissolved and solid dispersed particles by atomization of the liquid dispersion into the fluid bed, so as to deposit non-volatile components of the liquid dispersion as a solid coating layer on the core unit and,
c) removing volatile components of the liquid dispersion from the coated core unit.

For a description of suitable fluid-bed equipment, see, e.g., Harnby et al., *Mixing in the Process Industries*, pp. 54-77 (ISBN 0408-11574-2).

Formation and application of the coating may also be performed using techniques known per se in the art, e.g. a mechanical coating process.

The coating step, i.e. addition of the liquid dispersion/additional coatings to the core unit may be done as a pure mechanical coating process, wherein the core unit is mixed with the liquid dispersion/coating material in a mixer, such as in a Pan granulator, or as a fluid bed coating process in which the core unit is fluidised and the liquid dispersion/coating material is sprayed onto the core unit or a combined mechanical coating and a fluid bed coating process. Both of these processes can be utilised, e.g. first fluid bed coating to enhance the core unit size up to a certain minimum size followed by a mechanical layering process to reach the final size, or just one of them can be utilised.

A mechanical coating process may also be combined with a fluid bed drying step to enhance the production rate.

Applications of the Coated Granule

The coated granule according to the invention is useful where for example enzymes are to be stored alone or to be incorporated in another dry product, and improved enzyme stability is needed to enable good storage properties (improved shelf life) of the granule. The granule is especially suitable for storage at relatively high humid conditions. The granule is also particularly useful in dry products comprising oxidative compounds such as peroxides or superoxides, e.g. bleach (e.g. perborates or percarbonates) or other reactive components, which in case of contact with the enzyme is able of inactivating the enzyme. Thus the invention provides a detergent composition comprising the granule of the invention. The coated granule is also useful for cleaning an object (e.g. textile of cotton or other natural or synthetic fabrics) by contacting the object with an aqueous solution of the coated granule. Finally the coated granule is useful in products such as animal feed/fodder or bakers flour to improve bread as an additive in food or used in food compositions.

Detergent Disclosure

A detergent composition of the invention comprises the coated granule of the invention and a surfactant. Additionally, it may optionally comprise a builder, another enzyme, a suds suppresser, a softening agent, a dye-transfer inhibiting agent and other components conventionally used in detergents such as soil-suspending agents, soil-releasing agents, optical brighteners, abrasives, bactericides, tarnish inhibitors, coloring agents, and/or encapsulated or non-encapsulated perfumes.

The detergent composition according to the invention can be in bars or granular forms. The pH (measured in aqueous solution at use concentration) will usually be neutral or alkaline, e.g. in the range of 7-11.

An enzyme contained in the granule of the invention incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Surfactant System

The surfactant system may comprise nonionic, anionic, cationic, ampholytic, and/or zwitterionic surfactants. The surfactant system preferably consists of anionic surfactant or a combination of anionic and nonionic surfactant, e.g. 50-100% of anionic surfactant and 0-50% non-ionic. The laundry detergent compositions may also contain cationic, ampholytic, zwitterionic, and semi-polar surfactants, as well as the nonionic and/or anionic surfactants other than those already described herein.

The surfactant is typically present at a level from 0.1% to 60% by weight. Some examples of surfactants are described below.

a) Nonionic Surfactant:

The surfactant may comprise polyalkylene oxide (e.g. polyethylene oxide) condensates of alkyl phenols. The alkyl group may contain from about 6 to about 14 carbon atoms, in a straight chain or branched-chain. The ethylene oxide may be present in an amount equal to from about 2 to about 25 moles per mole of alkyl phenol.

The surfactant may also comprise condensation products of primary and secondary aliphatic alcohols with about 1 to about 25 moles of ethylene oxide. The alkyl chain of the aliphatic alcohol can either be straight or branched, and generally contains from about 8 to about 22 carbon atoms.

Further, the nonionic surfactant may comprise polyethylene oxide condensates of alkyl phenols, condensation products of primary and secondary aliphatic alcohols with from about 1 to about 25 moles of ethylene oxide, alkylpolysaccharides, and mixtures hereof. Most preferred are C8-C14 alkyl phenol ethoxylates having from 3 to 15 ethoxy groups and C8-C18 alcohol ethoxylates (preferably C10 avg.) having from 2 to 10 ethoxy groups, and mixtures thereof.

b) Anionic Surfactants:

Suitable anionic surfactants include the alkyl sulfate surfactants which are water soluble salts or acids of the formula ROSO3M wherein R preferably is a C10-C24 hydrocarbyl, preferably an alkyl or hydroxyalkyl having a C10-C20 alkyl component, more preferably a C12-C18 alkyl or hydroxyalkyl, and M is H or a cation, e.g., an alkali metal cation (e.g. sodium, potassium, lithium), or ammonium or substituted ammonium.

Other anionic surfactants include salts (including, for example, sodium, potassium, ammonium, and substituted ammonium salts such as mono- di- and triethanolamine salts) of soap, C8-C22 primary or secondary alkanesulfonates, C8-C24 olefinsulfonates, sulfonated polycarboxylic acids prepared by sulfonation of the pyrolyzed product of alkaline earth metal citrates.

Alkylbenzene sulfonates are suitacble, especially linear (straight-chain) alkyl benzene sulfonates (LAS) wherein the alkyl group preferably contains from 10 to 18 carbon atoms. The laundry detergent compositions typically comprise from about 1% to about 40%, preferably from about 3% to about 20% by weight of such anionic surfactants.

Builder System

The compositions according to the present invention may further comprise a builder system. Any conventional builder system is suitable for use herein including aluminosilicate materials, silicates, polycarboxylates and fatty acids, materials such as ethylenediamine tetraacetate (EDTA), metal ion sequestrants such as aminopolyphosphonates. Phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Detergency builder salts are normally included in amounts of from 5% to 80% by weight of the composition. Preferred levels of builder for liquid detergents are from 5% to 30%.

Bleaching Agents

The detergent composition may also comprise a bleaching agents, e.g. an oxygen bleach or a halogen bleach. The oxygen bleach may be a hydrogen peroxide releasing agent such as a perborate (e.g. PB1 or PB4) or a percarbonate, or it may e.g. be a percarboxylic acid. The particle size of a bleaching agent may be 400-800 microns. When present, oxygen bleaching compounds will typically be present at levels of from about 1% to about 25%.

The hydrogen peroxide releasing agent can be used in combination with bleach activators such as tetra-acetylethylenediamine (TAED), nonanoyloxybenzene-sulfonate (NOBS), 3,5-trimethyl-hexsanoloxybenzene-sulfonate (ISONOBS) or pentaacetylglucose (PAG).

The halogen bleach may be, e.g. a hypohalite bleaching agent, for example, trichloroisocyanuric acid and the sodium and potassium salt of dichloroisocyanurates and N-chloro and N-bromo alkane sulfonamides. Such materials are normally added at 0.5-10% by weight of the finished product, preferably 1-5% by weight.

Granular detergent compositions according to the present invention can also be in "compact form", i.e. they may have a relatively higher density than conventional granular detergents, i.e. form 550 to 950 g/l.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

More specifically, the enzyme containing granules of the invention may be incorporated in the detergent compositions described in WO 97/04079, WO 97/07202, WO 97/41212, and PCT/DK 97/00345.

MATERIALS AND METHODS

Example 1

A liquid dispersion was prepared by making a 2.5% Dextrin W80 and 26% $Na_2SO_4$ solution in water and adding an amount of a 17:3 kaolin (Speswhite):titan mixture equal to the sulphate, i.e. the final dispersion contain 21% $Na_2SO_4$ and 21% kaolin/titan (18% kaolin and 3% titan). Kaolin have particle sizes of 1-10 μm and titan have particle sizes of 0.1-1 μm. After dispersing the kaolin/titan in the sulphate solution, the dispersion comprising dissolved salt and dispersed particles were fed to a Huttlin fluid bed spray coater and atomised onto a preformed enzyme containing core unit prepared according to U.S. Pat. No. 4,106,991 example 1. The reference was prepared the same way without addition of kaolin/titan. The resulting percentage of sulphate and kaolin/titan on the particle is given relative to the uncoated enzyme core.

The stability of the coated granules was tested over a period of time in a detergent composition at fixed conditions. The stability of the coated granules was found to be approximately the same as for a conventional $Na_2SO_4$-coating without kaolin. However, the amount of water needed to be evaporated (and thus the spray time) for the coating comprising salt and kaolin/titan was approximately half of the spray time for the conventional coating: Water/kg solids in coating feed without kaolin/titan: 2.5 kg (71.5/26.0+2.5) Water/kg solids in coating feed with kaolin/titan: 1.3 kg (71.5/ (26.0+2.6+ 26.0)

Storage stability in a detergent (7 days at 40° C./60% RH):

| Salt coating | % residual activity |
|---|---|
| None | 39 |
| 20% $Na_2SO_4$ | 84 |
| 10% Kaolin/titan + 10% $Na_2SO_4$ | 73 |

The stability of the 10% Kaolin/titan + 10% $Na_2SO_4$ is nearly as good as 20% $Na_2SO_4$

Example 2

A liquid dispersion was prepared by dissolving 21.8 g $Na_2SO_4$ in 50 g, 40° C. $H_2O$. This solution was added 0.8 g Dextrin W-80 and 2.7 g Kaolin (Speswhite). To this dispersion additional 85.1 g dry milled $Na_2SO_4$ with a particle size of approx. 20 μm and 2.5 g sucrose was added.

The resulting dispersion was low viscous, stable and robust even during significant temperature variations found in the equipment (e.g. in tubes, pumps, nozzles etc.)

Enzyme containing core units were coated using this dispersion, without any problems with blocking of tubes nozzles or other equipment, indicating that formation of large salt crystals was avoided, despite the unusually high content of salt in the dispersion.

Stability of the granules in detergents:

| | Residual activity | |
|---|---|---|
| Detergent conditions | Conventionally coated Granule | Granule according to the invention |
| European automatic dish wash detergent/ 6 weeks 35/55% | 33% | 95% |
| Japanese laundry detergent/6 weeks 35/55% | 88% | 99% |

As can be seen from the results the coating as provided by the present invention is fully comparable to conventional coating. Hence the method of the invention does not impair the quality of the granule.

Example 3

Three different dispersions were prepared:

1. A liquid dispersion was prepared by dissolving 100 g of sodium tripolyphosphate ($Na_5P_3O_{10}$) and 200 g of sucrose in 3000 g 40° C. $H_2O$. This solution was added 6600 g of $Na_2SO_4$ and 100 g of Dextrin W-80. The dispersion was hereafter milled for approximately 4 hours in a 5 liter ball mill containing about 2 kg porcelain balls with a diameter of about 15 mm. The resulting dispersion was low viscous, stable and robust even during significant temperature variations found in the equipment (e.g. in tubes, pumps, nozzles etc.). The $Na_2SO_4$ was wet milled to a particle size of approx. 2 μm.

Enzyme containing core units were coated using this dispersion, without any problems with blocking of tubes nozzles or other equipment, indicating that formation of large salt crystals was avoided, despite the unusually high content of salt in the dispersion.

2. A liquid dispersion was prepared by dissolving 100 g of sodium tripolyphosphate ($Na_5P_3O_{10}$) and 200 g of sucrose in 3000 g 40° C. $H_2O$. This solution was added 6600 g of dry milled $Na_2SO_4$ with a particle size of approx. 20 μm and 100 g of Dextrin W-80. The result was a dispersion with a viscosity insignificant lower than the dispersion which was ball milled. Enzyme containing core units were coated using this dispersion, without any problems with blocking of tubes nozzles or other equipment.

3. A liquid solution was prepared, as a reference, by dissolving 50 g of sodium tripolyphosphate ($Na_5P_3O_{10}$) and 100 g of sucrose in 6800 g 40 °C. $H_2O$. This solution was added 3000 g of $Na_2SO_4$ and 50 g of Dextrin W-80.

The $Na_2SO_4$ was completely dissolved and the result was a low viscous, stable and robust dispersion.

Enzyme containing core units were coated using this dispersion, without any problems.

The enzymatic stability of the prepared granules was tested against the reference in an accelerated stability test:

| Batches | Water evaporated per kg coating dry matter (kg/kg) | Residual activity (normalized with reference) |
|---|---|---|
| Coated with dispersion 1 | 0.43 | 75% |
| Coated with dispersion 2 | 0.43 | 65% |
| Coated with the reference coating | 2.13 | 100% |

The results show that a significantly improved storage stability is obtained when the dispersion is wet milled and that the amount of water evaporated pr. kg of added coating layer is nearly 5 times less for dispersion 1 and 2 as compared to the reference. Consequently, it is possible to obtain good storage stability and excellent energy efficiency using the present invention.

The invention claimed is:

1. A process for preparing a coated granule comprising the steps of:

a) providing a core unit comprising an enzyme;

b) contacting the core unit with a liquid dispersion comprising a solvent, a dissolved salt and solid dispersed particles wherein the solid dispersed particles are selected from constituents selected from the group consisting of salt and starch, wherein the liquid dispersion is saturated with salt, and wherein the solid dispersed particles constitute at least 10% w/w of the total dry matter of the liquid dispersion; and c) evaporating the solvent of the liquid dispersion to leave salt and solid particles coated onto the core unit.

2. A process according to claim 1 wherein the core unit comprises an enzyme layered over an inert core particle.

3. A process according to claim 1, wherein the liquid dispersion has a dry matter content in the range of 10-90% w/w.

4. A process according to claim 1 wherein the liquid dispersion is substantially enzyme free.

5. A process according to claim 1, wherein the solubility of the dissolved salt is above 0.1 g/liter.

6. A process according to claim 1, wherein at least part of the solid dispersed particles are the same salt as the dissolved salt.

7. A process according to claim 1, wherein the dissolved salt is selected among the group consisting of $NaH_2PO_4$, $Na_2HPO_4$, $Na_3PO_4$, $(NH_4)H_2PO_4$, $KH_2PO_4$, $K_2HPO_4$, $Na_2SO_4$, $K_2SO_4$, $KHSO_4$, $ZnSO_4$, $MgSO_4$, $CuSO_4$, $Mg(NO_3)_2$, $(NH_4)_2SO_4$, sodium borate, magnesium acetate, sodium citrate, magnesium sulfate heptahydrate ($MgSO_4(7H_2O)$), zinc sulfate heptahydrate ($ZnSO_4(7H_2O)$), copper sulfate pentahydrate ($CuSO_4(5H_20)$), sodium phosphate dibasic heptahydrate ($Na_2HPO_4(7H_20)$), magnesium nitrate hexahydrate ($Mg(NO_3)_2(6H_20)$), sodium borate decahydrate, sodium citrate dihydrate and magnesium acetate tetrahydrate.

8. A process according to claim 1, wherein the solid dispersed particles have a size in the longest dimension less than the thickness of the coating, such as less than 20 microns, or less than 10 microns, or less than 5 microns or less than 2 microns such as less than 1 micron.

9. A process according to claim 1, wherein the solid dispersed particles constitutes at least one salt.

10. A process according to claim 1, wherein the solid dispersed particles are selected among the group consisting of $NaH_2PO_4$, $Na_2HPO_4$, $Na_3PO_4$, $(NH_4)H_2PO_4$, $KH_2PO_4$, $K_2HPO_4$, $Na_2SO_4$, $K_2SO_4$, $ZnSO_4$, $MgSO_4$, $CuSO_4$, $Mg(NO_3)_2$, $(NH_4)_2SO_4$,$CaCO_3$, sodium borate, magnesium acetate, sodium citrate, magnesium sulfate heptahydrate ($MgSO_4(7H_2O)$), zinc sulfate heptahydrate ($ZnSO_4(7H_2O)$), copper sulfate pentahydrate ($CuSO_4(5H_20)$), sodium phosphate dibasic heptahydrate ($Na_2HPO_4(7H_20)$), magnesium nitrate hexahydrate ($Mg(NO_3)_2(6H_20)$), sodium borate decahydrate, sodium citrate dihydrate and magnesium acetate tetrahydrate.

11. A process according to claim 1 wherein the dispersion is prepared by (1) preparing a saturated solution of a desired salt and (2) adding a sufficient amount of solid particles to be dispersed.

12. A process according to claim 1 wherein the liquid dispersion is prepared by wet milling.

13. A process according to claim 1 wherein the coating of the core unit, step b) is performed in a fluid bed, mixer, pan granulator, coating drum.

14. A process according to claim 1, wherein the core unit is a spray drying product, a layered product, an absorbed core particle, an extrusion or pelletized product, a prilled product or a mixer granulation product, a melt granulation product or a high shear granulation product.

15. A process according to claim 1 comprising further steps of coating.

16. A process for preparing a coated granule comprising the steps of: a) providing a core unit comprising an enzyme; b) contacting the core unit with a liquid dispersion comprising a solvent, a dissolved salt and solid salt dispersed particles wherein the liquid dispersion is saturated with salt, and wherein the solid salt dispersed particles constitute at least 10% w/w of the total dry matter of the liquid dispersion; and c) evaporating the solvent of the liquid dispersion to leave salt and solid particles coated onto the core unit.

* * * * *

UNITED STATES PATENT AND TRADEMARK OFFICE

CERTIFICATE OF CORRECTION

PATENT NO. : 7,632,799 B2
APPLICATION NO. : 11/442649
DATED : December 15, 2009
INVENTOR(S) : Bach et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this

Second Day of November, 2010

David J. Kappos

*Director of the United States Patent and Trademark Office*